United States Patent
Jung et al.

(10) Patent No.: US 10,151,705 B2
(45) Date of Patent: Dec. 11, 2018

(54) METHOD OF GENERATING A COMPENSATION MATRIX DURING A SUBSTRATE INSPECTION

(71) Applicant: KOH YOUNG TECHNOLOGY INC., Seoul (KR)

(72) Inventors: Seungwon Jung, Seoul (KR); Jongjin Choi, Gwangmyeong-si (KR); Heewook You, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/021,341

(22) PCT Filed: Sep. 11, 2014

(86) PCT No.: PCT/KR2014/008471
§ 371 (c)(1),
(2) Date: Mar. 11, 2016

(87) PCT Pub. No.: WO2015/037917
PCT Pub. Date: Mar. 19, 2015

(65) Prior Publication Data
US 2016/0223468 A1    Aug. 4, 2016

(30) Foreign Application Priority Data
Sep. 12, 2013 (KR) .................. 10-2013-0109907

(51) Int. Cl.
*G01N 21/00* (2006.01)
*G01N 21/88* (2006.01)
*G01N 21/956* (2006.01)
(Continued)

(52) U.S. Cl.
CPC ....... *G01N 21/8851* (2013.01); *G01N 21/956* (2013.01); *G01N 21/95607* (2013.01);
(Continued)

(58) Field of Classification Search
CPC .......... G06T 7/001; G06T 2207/30141; G06K 9/6203; G01N 21/95607; H05K 13/08
(Continued)

(56) References Cited

U.S. PATENT DOCUMENTS 7,385,689 B2 * 6/2008 Kim ................. G01N 21/21
356/237.4
9,911,185 B2 * 3/2018 Jung .................... G06T 7/0004
(Continued)

FOREIGN PATENT DOCUMENTS

EP   0 206 709    12/1986
JP   7-49313      2/1995
(Continued)

OTHER PUBLICATIONS

International Search Report for International Application No. PCT/KR2014/008471, dated Oct. 28, 2014.

*Primary Examiner* — Hoa Pham
(74) *Attorney, Agent, or Firm* — Kile Park Reed & Houtteman PLLC

(57) ABSTRACT

The present invention relates to a method for generating a compensation matrix during a substrate inspection. The method comprises the steps of: selecting information of N1 (N1≥2) feature objects which are randomly predetermined within a field of view (FOV) on a substrate; generating a first compensation matrix on the basis of information of the feature objects which are extracted on the substrate; comparing an offset value of each of all the feature objects with a predetermined reference value by applying all the feature objects within the FOV to the compensation matrix to count the number of the feature objects of which the offset value of the each of all the feature objects is less than the predetermined reference value; and repeatedly performing the above steps N2 times (N2≥1), and generating a second compensation matrix using information of the feature
(Continued)

objects which have the offset value which is less than the predetermined reference value, in case the number of the counted feature objects is the maximum.

6 Claims, 3 Drawing Sheets

(51) Int. Cl.
  *G06T 5/00* (2006.01)
(52) U.S. Cl.
  CPC ....... *G01N 21/95684* (2013.01); *G06T 5/006* (2013.01); *G01N 2021/8896* (2013.01); *G01N 2021/95638* (2013.01); *G01N 2201/121* (2013.01); *G06T 2207/20076* (2013.01); *G06T 2207/30141* (2013.01)
(58) Field of Classification Search
  USPC .......................................... 356/237.1–237.5
  See application file for complete search history.

(56) References Cited

U.S. PATENT DOCUMENTS

| | | | |
|---|---|---|---|
| 2005/0030305 A1* | 2/2005 | Brown | G02B 26/0841 345/207 |
| 2012/0123719 A1* | 5/2012 | Hwang | G01B 11/24 702/85 |
| 2012/0130666 A1 | 5/2012 | Cho et al. | |
| 2016/0225129 A1* | 8/2016 | Jung | G06T 7/0004 |

FOREIGN PATENT DOCUMENTS

| | | |
|---|---|---|
| JP | 2006-58294 | 3/2006 |
| JP | 2011-95226 | 5/2011 |
| KR | 10-2012-0051806 | 5/2012 |
| WO | 02/39326 | 5/2002 |

* cited by examiner

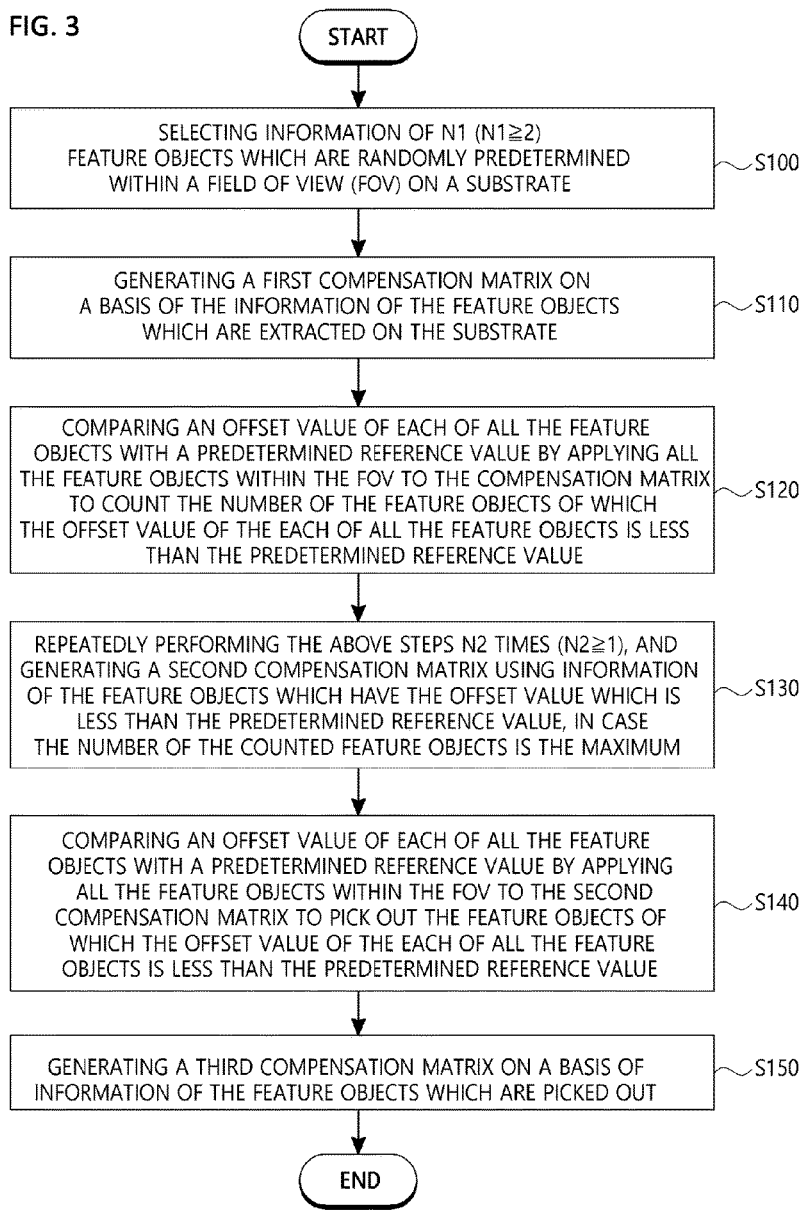

METHOD OF GENERATING A COMPENSATION MATRIX DURING A SUBSTRATE INSPECTION

TECHNICAL FIELD

The present invention relates to a method of generating a compensation matrix during a substrate inspection. More particularly, the present invention relates to a method of generating a compensation matrix during a substrate inspection in which feature objects consistent with the compensation matrix are extracted and effectiveness of the generated compensation matrix.

BACKGROUND ART

In general, an electronic device includes at least one printed circuit board (PCB), on which circuit patterns, connection pads, driving chips electrically connected to the connection pads, etc. are formed.

In general, in order to inspect the PCB if the driving chips are mounted properly, a shape measuring apparatus is used.

A conventional shape measuring apparatus sets a field of view (FOV) and inspects the FOV if a circuit device is properly formed in the FOV.

In order to inspect the circuit device exactly, the FOV in which the circuit device is mounted should be set exactly. However, an objection target such as a PCB can be warped or distorted, etc. Therefore, warpage or distortion should be compensated.

In order for that, the position of a pad in a FOV can be compensated by a compensation matrix generated by a feature object such as a curved pattern, a hole pattern, etc. In this case, the reliability of the compensation matrix is important. Therefore, a method of generating a compensation matrix, which is capable of improving the reliability thereof, is requested.

DISCLOSURE

Technical Problem

In order to solve the technical problem, the object of the present invention is to provide a method of generating a compensation matrix during a substrate inspection for determining the effectiveness of the compensation matrix generated by feature objects consistent with the compensation matrix when a compensation matrix is generated by using feature objects in the present FOV.

The object of the present invention is not limited by above, and other objects not mentioned above will be clearly understood by a person skilled in the art through the following descriptions.

Technical Solution

A method of generating a compensation matrix during a substrate inspection according to an embodiment of the present invention, comprises selecting information of N1 (N1≥2) feature objects which are randomly predetermined within a field of view (FOV) on a substrate, generating a first compensation matrix on a basis of information of the feature objects which are extracted on the substrate, comparing an offset value of each of all the feature objects with a predetermined reference value by applying all the feature objects within the FOV to the compensation matrix to count the number of the feature objects of which the offset value of the each of all the feature objects is less than the predetermined reference value, and repeatedly performing the above steps N2 times (N2≥1), and generating a second compensation matrix using information of the feature objects which have the offset value which is less than the predetermined reference value, in case the number of the counted feature objects is the maximum.

The method may further comprise comparing an offset value of each of all the feature objects with the predetermined reference value by applying all the feature objects within the FOV to the second compensation matrix to pick out the feature objects of which the offset value of the each of all the feature objects is less than the predetermined reference value, and generating a third compensation matrix on a basis of information of the feature objects which are picked out.

The first compensation matrix and the second compensation matrix may be one of an affine transformation matrix or a projective transformation matrix.

In this case, the N2 may be determined by following equation, $$N2 = \frac{\log(1-p)}{\log(1-u^{N1})}$$

wherein 'p' is a probability of selecting only feature objects of which offset value are less than the specific offset value when N1 feature objects are selected, and 'u' is a probability of being a feature object of which offset value is less than the specific offset value when one feature object is selected.

The feature object may be at least one of a hole pattern, a circle pattern and a corner portion of a curved pattern.

The above methods may be stored in a computer-readable media.

Advantageous Effects

According to the method of generating a compensation matrix during a substrate inspection, a reliability of a compensation matrix can be enhanced in generating a compensation matrix for compensating a position of a pad for substrate inspection, so that the precision of substrate inspection can be enhanced.

The advantageous effects are not limited by above description, and other advantageous effects not described above may be understood by a person skilled in the art through the following descriptions.

DESCRIPTION OF DRAWINGS

FIG. 3 is a flow chart showing a method of compensating a FOV during a substrate inspection according to an embodiment of the present invention.

MODE FOR INVENTION

The objects, the effects and the technical features of the present invention for obtaining them will be clearer with reference to the accompanying embodiments and drawings. In explaining the present invention, explanation of well-known function or structure, etc. that may get out of the point will be omitted. The terminology used herein is defined in consideration of a structure, a role, a function, etc. and may be changed according to an intention of a user or a practice.

However, the present invention may be embodied in many different forms and should not be construed as limited to the example embodiments set forth herein. Rather, these example embodiments are provided so that this disclosure will be thorough and complete, and will fully convey the scope of the present invention to those skilled in the art, and the present invention should be limited by claims. Therefore, the definition should be understood throughout the specification.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, with reference to the drawings, preferred embodiments of the present invention will be described in detail.

Figure 1:
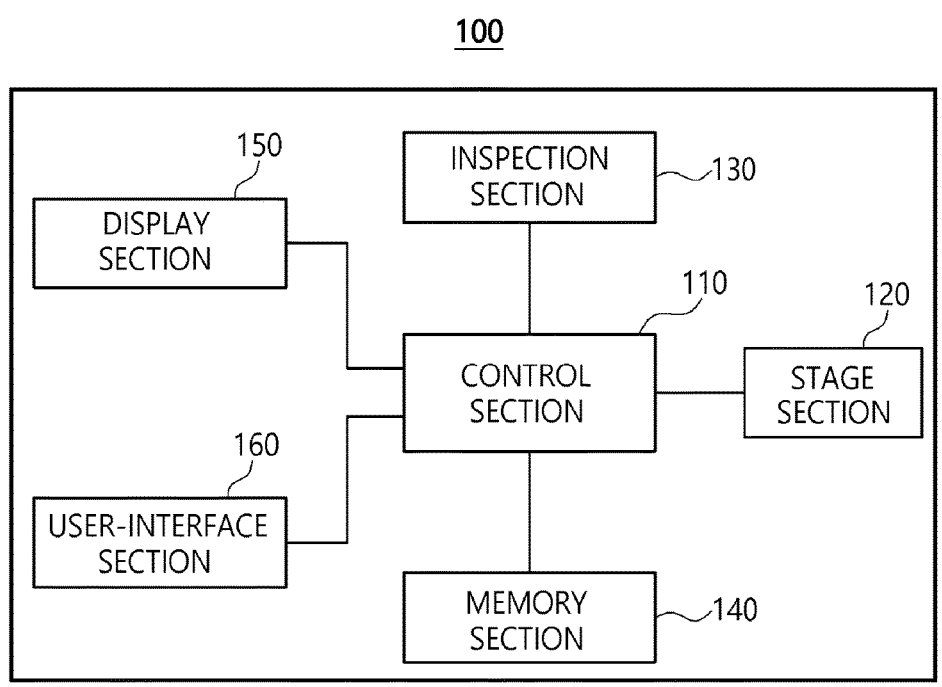
FIG. 1 is a block diagram showing a substrate inspection apparatus for performing a method of compensating a field of view (FOV) during a substrate inspection according to an embodiment of the present invention.

FIG. 1 is a block diagram showing a substrate inspection apparatus for performing a method of compensating a field of view (FOV) during a substrate inspection according to an embodiment of the present invention.

Referring to FIG. 1, a substrate inspection apparatus 100 may include a control section 110 controlling the substrate inspecting apparatus 100 and performing calculation for various function, a stage section 120 supporting and moving an inspection target substrate, an inspection section 130 inspecting the substrate supported by the stage section 120, a memory section 140 storing a program for driving the substrate inspection apparatus 100 and data, a display section 150 displaying and outputting the operation status of the substrate inspection apparatus 100 and the inspection result, and an user-interface section 160 receiving a user input.

First, a field of view (FOV) is set on a substrate, in order for setting an inspection region for inspecting the substrate. The FOV means a region of a substrate, for inspecting the substrate, and a plurality of FOVs may be set on the substrate. The FOV may be set based on an image-capturing range of a camera included in the inspection section 130.

Then, a reference data regarding to the FOV is obtained. The reference data may be, for example, a theoretical plane image of the substrate. The reference data may be obtained from a CAD information recording the shape of the substrate or a gerber information. The CAD information or the gerber information includes a design reference information of the substrate, and includes, in general, position information of a pad, a circuit pattern, a hole pattern, etc.

On the other hand, the reference data may be obtained from a study information obtained by a study mode. In the study mode, the substrate information is searched in the memory section 140, a bare substrate is studied when there exists no substrate information as result of the search, and the substrate information such as a pad and wiring information is obtained as a result of the study of the bare substrate to be stored in a database. That is, in the study mode, a design reference information of the substrate is obtained by studying the bare substrate of a printed circuit board, and the reference data may be obtained by the study information obtained in the study mode.

Then, a measurement data regarding the FOV is obtained. The measurement data may be an image of the substrate corresponding to the reference data, which is captured by the substrate inspection apparatus 100. The measurement data is similar to the reference data, but may be distorted by warpage or distortion of the substrate.

Therefore, in order to compensate of the distortion, a compensation matrix may be obtained by using the coordinates of feature objects in FOV and the position of pad in the FOV may be compensated by using the compensation matrix. The feature objects may be at least one of a hole pattern, a circle pattern, a corner section of a curved pattern, etc.

In this case, the feature objects are selected in the FOV, and the compensation matrix is generated by using the information of the feature objects. Some of the feature objects may have different tendency from other feature objects. As the compensation matrix includes more feature objects with different tendency, the reliability of the compensation matrix is lowered to lower the reliability of compensation.

In order to solve above problem, an embodiment of the present invention uses the following algorithm in order to generate a compensation matrix by using feature object information, which is obtained by feature objects suitable for the compensation matrix.

Figure 2:
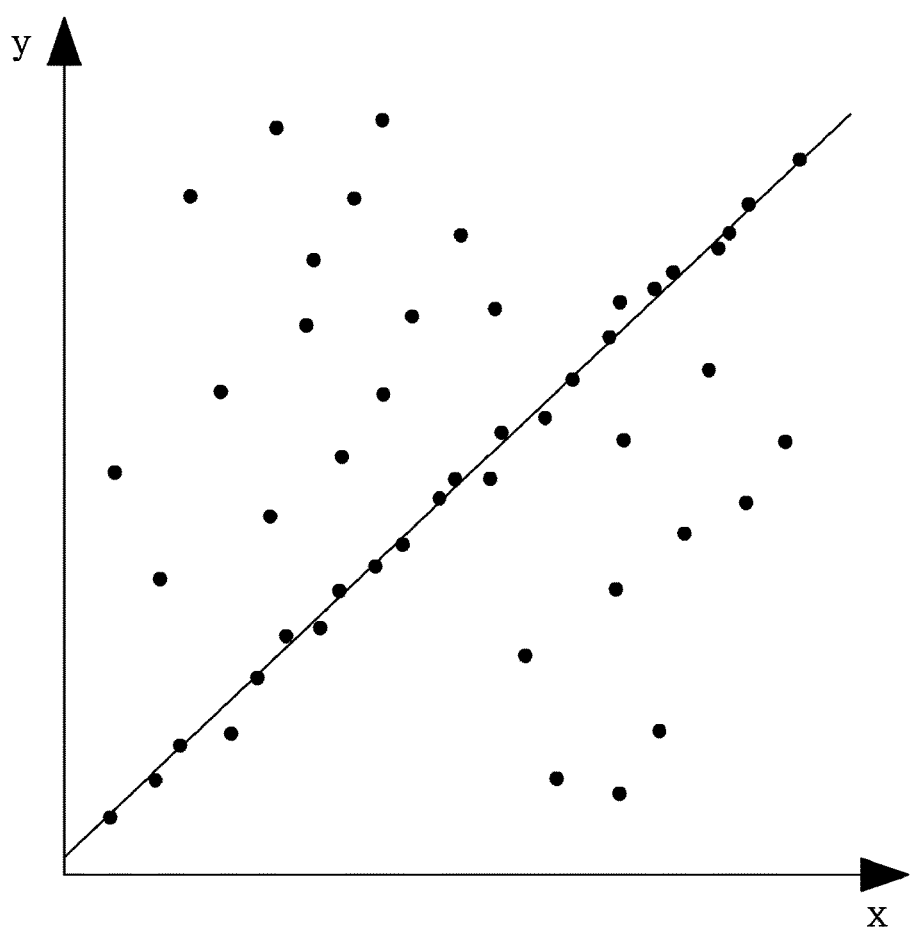
FIG. 2 is a figure for explaining an algorithm for applying a method of compensating a FOV during a substrate inspection according to an embodiment of the present invention.

FIG. 2 is a figure for explaining an algorithm for applying a method of compensating a FOV during a substrate inspection according to an embodiment of the present invention.

When a mathematical model is generated by using a portion of data set under the assumption that the data set includes true information (inlier), information that is not suitable for the model (outlier) may exist. The points with blue color correspond to points suitable for the mathematical model, and the point with red color correspond to point not suitable for the mathematical model in FIG. 2. In this case, a model which can be calculated by the true information can be generated when the amount of the true information (inlier) is enough.

FIG. 3 is a flow chart showing a method of compensating a FOV during a substrate inspection according to an embodiment of the present invention.

As shown in FIG. 3, information of N1 (N1≥2) feature objects which are randomly predetermined within a field of view (FOV) on a substrate is selected (S100). The number of the feature objects that will be selected can be set by the substrate inspection apparatus 100. In this case, the feature objects are randomly selected, and all algorithms for randomly selecting the feature objects can be applied.

Then, a first compensation matrix is generated on a basis of the information of the feature objects which are extracted on the substrate (S110). In this case, the first compensation matrix may be an affine transformation matrix or a projective transformation matrix.

And, an offset value of each of all the feature objects is compared with a predetermined reference value by applying all the feature objects within the FOV to the compensation matrix to count the number of the feature objects of which the offset value of the each of all the feature objects is less than the predetermined reference value (S120). The offset value of each of all the feature objects can be obtained by applying all the feature objects within the FOV to the compensation matrix. In this case, when an offset value is less than the predetermined reference value, the feature object corresponding to the offset value is considered to be an effective feature object that ties in with the compensation matrix. In this case, the predetermined value can be set by minimum pixel unit, and, for example, may have a value of one or two.

Then, the above steps (S100~S120) are repeatedly performed N2 times (N2≥1), and a second compensation matrix is generated by using information of the feature objects which have the offset value which is less than the predetermined reference value, in case the number of the counted feature objects is the maximum (S130). The above steps are repeatedly performed N2 times to find out a compensation matrix with a maximum number of feature objects having the offset value less than the predetermined reference value, and the second compensation matrix is generated by using the information of the feature objects having the offset value less than the predetermined reference value in the compensation matrix.

In this case, the N2 can be determined by the following Expression 1.

$$N2 = \frac{\log(1-p)}{\log(1-u^{N1})},\qquad \text{Expression 1}$$

wherein 'p' is a probability of selecting only feature objects of which offset value are less than the specific offset value when N1 feature objects are selected, and 'u' is a probability of being a feature object of which offset value is less than the specific offset value when one feature object is selected.

The second compensation matrix can be a final compensation matrix, but the following processes may be performed in order to improve reliability of a compensation matrix.

That is, an offset value of each of all the feature objects is compared with the predetermined reference value by applying all the feature objects within the FOV to the second compensation matrix to pick out the feature objects of which the offset value of the each of all the feature objects is less than the predetermined reference value (S140).

Then, a third compensation matrix is generated on a basis of information of the feature objects which are picked out (S150).

As described above, the reliability of the compensation matrix and the precision of the substrate inspection can be improved by generating the compensation matrix on a basis of the information of the feature objects suitable for the compensation matrix model.

The method of generating a compensation matrix during a substrate inspection can be stored embodied in a computer program which can be performed by various computers and stored in a computer-readable media. The computer-readable media may store program instructions, data files, data structures, etc., separately or in combination. The program instructions may be specially designed or structured but may include well-known algorithm. The computer-readable media may include a magnetic media such as a hard disk, a floppy disk and a magnetic tape, an optical media such as a CD-ROM and a DVD, a magneto-optical media such as a floptical disk, and a hardware device such as a ROM, a RAM and a flash memory, which is capable of storing and performing program instructions. The examples of the program include not only a machine language code generated by a compiler but also a high level language performed by a computer using an interpreter.

According to the FOV compensation method during a substrate inspection, when a compensation matrix generated by the information of the feature objects in the present FOV is under low reliability, a compensation matrix is generated by using feature objects in a neighboring FOV to improve reliability of the substrate inspection result regarding to the present FOV.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A method of compensating position information of a field of view (FOV) on a substrate during a substrate inspection by a substrate inspection apparatus, the method comprising:
   determining the FOV based on an image-capturing range of a camera of the substrate inspection apparatus;
   selecting, by a computer and a computer program, feature objects within the FOV of the substrate;
   generating, by the computer and the computer program, a first compensation matrix on a basis of information of the selected feature objects within the FOV and storing the first compensation matrix in a memory section;
   obtaining an offset value of each of the selected feature objects within the FOV by applying the selected feature objects to the first compensation matrix and storing the offset value in the memory section;
   comparing, by the computer and the computer program, offset values of the selected feature objects with reference values of the selected feature objects;
   obtaining effective feature objects from the selected feature objects within the FOV, wherein the effective feature objects are ones of the selected feature objects of which offset values are less than the reference values thereof;
   repeatedly performing, by the computer and the computer program, the above steps N times (N≥1) on the FOV to count a number of effective feature objects in each time and determine a maximum number among counted numbers at the N times;
   generating, by the computer and the computer program, a second compensation matrix using information of effective feature objects of which number is determined as the maximum number and storing the second compensation matrix in the memory section;
   compensating, by the computer and the computer program, the position information of the FOV on the substrate with the second compensation matrix to be same as position information of an exact area intended to be inspected; and
   a display section that displays operation status and result of the substrate inspection by the substrate inspection apparatus.

2. The method of claim 1, further comprising:
   (a) obtaining an offset value of each of the selected feature objects by applying the selected feature objects to the second compensation matrix;
   (b) comparing, by the computer and the computer program, offset values obtained in step (a) with the reference values of the selected feature objects;
   (c) obtaining effective feature objects from the selected feature objects, the effective feature objects having offset values less than the reference values thereof;
   (d) repeatedly performing steps (a) through (c) M times (M≥1) on the FOV to count a number of effective feature objects in each time and determine a maximum number among counted numbers at the M times;

(e) generating, by the computer and the computer program, a third compensation matrix on a basis of information of effective feature objects of which number is determined as the maximum number in step (d); and (f) compensating the position information of the FOV on the substrate with the third compensation matrix.

3. The method of claim 1, wherein the first compensation matrix and the second compensation matrix are one of an affine transformation matrix or a projective transformation matrix.

4. The method of claim 1, wherein the N is determined by following equation, $$N2 = \frac{\log(1-p)}{\log(1-u^{N1})}$$

wherein 'p' is a probability of selecting only feature objects of which offset values are less than the specific offset values when N1 feature objects are selected, and 'u' is a probability of being a feature object of which offset value is less than the specific offset value when one feature object is selected.

5. The method of claim 1, wherein the feature object is at least one of a hole pattern, a circle pattern and a corner portion of a curved pattern.

6. A non-transitory computer-readable media storing program instructions for performing a computer implemented method for compensating position information of a field of view (FOV) on a substrate during a substrate inspection by a substrate inspection apparatus, wherein the computer implemented method comprises:

determining the FOV based on an image-capturing range of a camera of the substrate inspection apparatus;

selecting, by a computer and a computer program, feature objects within the FOV of the substrate;

generating, by the computer and the computer program, a first compensation matrix on a basis of information of the selected feature objects within the FOV and storing the first compensation matrix in a memory section;

obtaining an offset value of each of the selected feature objects within the FOV by applying the selected feature objects to the first compensation matrix and storing the offset value in the memory section;

comparing, by the computer and the computer program, offset values of the selected feature objects with reference values of the selected feature objects;

obtaining effective feature objects from the selected feature objects within the FOV, wherein the effective feature objects are ones of the selected feature objects of which offset values are less than the reference values thereof;

repeatedly performing, by the computer and the computer program, the above steps N times (N≥1) on the FOV to count a number of effective feature objects in each time and determine a maximum number among counted numbers at the N times;

generating, by the computer and the computer program, a second compensation matrix using information of effective feature objects of which number is determined as the maximum number and storing the second compensation matrix in the memory section;

compensating, by the computer and the computer program, the position information of the FOV on the substrate with the second compensation matrix to be same as position information of an exact area intended to be inspected; and a display section that displays operation status and result of the substrate inspection by the substrate inspection apparatus.

* * * * *